United States Patent [19]

Gramlich et al.

[11] Patent Number: 4,784,985

[45] Date of Patent: Nov. 15, 1988

[54] SUBSTITUTED 4-METHYL-4,7-DIHYDRO-1,3-DIOXEPINS, THEIR PREPARATION AND THEIR USE AS SCENTS

[75] Inventors: Walter Gramlich, Edingen-Neckarhausen; Hardo Siegel, Speyer, both of Fed. Rep. of Germany

[73] Assignee: BASF Aktiengesellschaft, Rheinland-Pfalz, Fed. Rep. of Germany

[21] Appl. No.: 923,214

[22] Filed: Oct. 27, 1986

[30] Foreign Application Priority Data

Nov. 7, 1985 [DE] Fed. Rep. of Germany ....... 3539467

[51] Int. Cl.$^4$ .............................................. A61K 7/46
[52] U.S. Cl. ........................................ 512/25; 512/22
[58] Field of Search ................................... 512/22, 25

[56] References Cited

U.S. PATENT DOCUMENTS

| | | | |
|---|---|---|---|
| 3,117,134 | 1/1964 | Sterling et al. | 549/347 |
| 3,822,290 | 7/1974 | Tavares et al. | 549/347 |
| 3,822,291 | 7/1974 | Tavares et al. | 549/347 |
| 3,908,023 | 9/1975 | Shreiber et al. | 512/22 |
| 3,985,769 | 10/1976 | Vesley et al. | 549/347 |
| 4,031,140 | 6/1977 | Schreiber et al. | 549/347 |
| 4,248,787 | 2/1981 | Sprecket et al. | 260/338 |

FOREIGN PATENT DOCUMENTS

| | | | |
|---|---|---|---|
| 2821011 | 11/1978 | Fed. Rep. of Germany | 512/25 |
| 7111071 | 2/1973 | Netherlands | 512/25 |

OTHER PUBLICATIONS

Chemical Abstract 69 1999 a (1968).
Chemical Abstracts, vol. 66:55590K (1967).

*Primary Examiner*—Werren B. Lone
*Attorney, Agent, or Firm*—Oblon, Fisher, Spivak, McClelland & Maier

[57] ABSTRACT

Substituted 4-methyl-4,7-dihydro-1,3-dioxepins of the general formula I

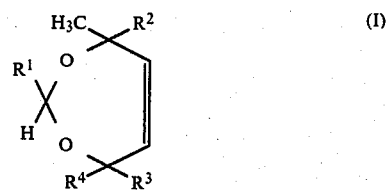

where $R^1$ is an alkyl of 1 to 12 carbon atoms which may furthermore contain oxygen in the form of an ether group, or a 5-membered to 8-membered ring which is unsubstituted or substituted by alkyl groups and/or an alkylene group, has up to 10 carbon atoms and may furthermore contain oxygen in the form of an ether group, and $R^2$, $R^3$ and $R^4$ are each hydrogen or methyl, with the exception of the compound 2-tert-butyl-4,7-dihydro-4,7-dimethyl-1,3-dioxepin, the preparation of substituted 4-methyl-4,7-dihydro-1,3-dioxepins and their use as scents and aromas, and scent compositions containing these compounds.

2 Claims, No Drawings

SUBSTITUTED 4-METHYL-4,7-DIHYDRO-1,3-DIOXEPINS, THEIR PREPARATION AND THEIR USE AS SCENTS

The present invention relates to substituted 4-methyl-4,7-dihydro-1,3-dioxepins of the general formula I

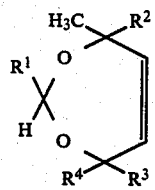

where $R^1$ is a straight-chain or branched alkyl radical of 1 to 12 carbon atoms which may furthermore contain oxygen in the form of an ether group, or is a 5-membered to 8-membered ring which is unsubstituted or substituted by alkyl groups and/or an alkylene group, has not more than 10 carbon atoms and may furthermore contain oxygen in the form of an ether group, and is preferably a straight-chain or branched alkyl radical of 1 to 6 carbon atoms, and $R^2$, $R^3$ and $R^4$ are each hydrogen or methyl, the total number of carbon atoms being not more than 25, with the exception of the compound 2-tert-butyl-4,7-dihydro-4,7-dimethyl-1,3-dioxepin.

Because of the general lack of availability of many natural scent components, the necessity of adapting to changing tastes in fashion and a steadily growing demand for odor improvers for products in daily use, such as cleaning agents, cosmetics, glues, etc., the scent industry is in constant need of novel scents which, alone or in the form of compositions, constitute useful perfumes or fragrance materials with interesting notes. Because little is known about the relationships between structure and fragrance properties, the selective synthesis of scents having the desired olfactory properties is not possible; hence, it is necessary to provide compounds which have useful fragrance properties.

We have found, by chance, that the compounds described above, of the formula I, ie. 4,7-dihydro-1,3-dioxepins which are substituted in the 2-position and possess one or more methyl groups in the 4- or 7-position, constitute a novel class having very interesting notes.

4,7-Dihydro-1,3-dioxepins (1,3-dioxa-5-cyclohexenes) of the formula IV

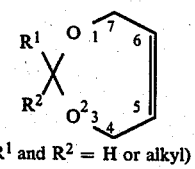

($R^1$ and $R^2$ = H or alkyl)

which are mono- or dialkylated in the 2-position are disclosed in the literature (see M. J. Soulier et al. Bull. Soc. Chim. Fr. 1975, pages 1763–1766) as herbicides and polymerization catalysts and as intermediates for scents (see European Patent No. 24,473). These compounds themselves do not possess any interesting olfactory properties and are not mentioned as scents in the stated publication (loc. cit.).

Furthermore, 4,7-dimethyl-4,7-dihydro-1,3-dioxepin and 2-tert-butyl-4,7-dimethyl-4,7-dihydro-1,3-dioxepin are known from the publication on conformational analyses in J. Org. Chem. 40, No. 4 (1975), 450–453. The publication does not contain any statements about possible fragrance properties.

Moreover, 4,4,7,7-tetramethyl-4,7-dihydro-1,3-dioxepin and 4,7-dimethyl-4,7-diethyl-4,7-dihydro-1,3-dioxepin which are unsubstituted in the 2-position are disclosed in CA69: P19996a as components for the preparation of copolymers. The last-mentioned publications too give no indication at all that compounds having the 1,3-dioxepin structure may be of interest as scents.

It was therefore very surprising that the novel 4-methyl-4,7-dihydro-1,3-dioxepins are compounds which have very interesting notes and can therefore be used as scents.

The application therefore also relates to the use of the substituted 4-methyl-4,7-dihydro-1,3-dioxepins of the general formula I

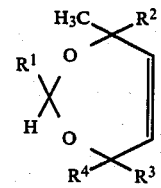

where $R^1$ is a straight-chain or branched alkyl radical of 1 to 12 carbon atoms which may furthermore contain oxygen in the form of an ether group, or is a 5-membered to 8-membered ring which is unsubstituted or substituted by alkyl groups and/or an alkylene group, has up to 10 carbon atoms and may furthermore contain oxygen in the form of an ether group, preferably a straight-chain or branched alkyl radical of 1 to 6 carbon atoms, and $R^2$, $R^3$ and $R^4$ are each hydrogen or methyl, the total number of carbon atoms being not more than 25, as scents and aromas, and scent compositions containing these substituted 4-methyl-4,7-dihydro-1,3-dioxepins.

The application furthermore relates to a process for the preparation of 4-methyl-4,7-dihydro-1,3-dioxepins of the general formula I, where $R^1$, $R^2$, $R^3$ and $R^4$ have the above meanings, wherein an aldehyde of the general formula II

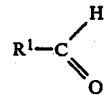

where $R^1$ has the above meanings, or one of its acetals, is subjected to a cyclization reaction with an alkenediol of the general formula III

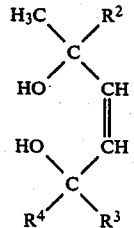

where $R^2$, $R^3$ and $R^4$ have the above meanings, in the presence or absence of an acidic catalyst.

Examples of suitable aldehydes of the general formula II are acetaldehyde, propionaldehyde, 2-methylpropanal, n-butyraldehyde, 2-methylbutanal, 3-methylbutanal, 2-ethylbutanal, valeraldehyde, 2-methylpentanal, 3-methylpentanal, 4-methylpentanal, 2,2-dimethylpropanal (pivalaldehyde) and unsubstituted higher aldehydes, such as n-hexanal, n-heptanal, n-octanal, n-nonanal, decanal and their monoalkylated and/or polyalkylated derivatives; the most well known members of this group are the large-scale chemical product 2-ethylhexanal and 3,5,5-trimethylhexanal.

Instead of the aldehyde, it is also possible to use the corresponding acetals, such as dimethylacetal. In most cases, however, the carbonyl compound can be used as the starting material.

Examples of suitable alkenediols of the general formula III are pent-2-ene-1,4-diol, 4-methylpent-2-ene-1,4-diol, hex-3-ene-2,5-diol, 2-methylhex-3-ene-2,5-diol and 2,5-dimethylhex-3-ene-2,5-diol. All alkenediols are readily obtainable from the correspondingly alkynediols by partial hydrogenation. The alkynediols are either themselves important chemical intermediates or can be readily obtained by reacting acetylene with the corresponding carbonyl compounds.

Cyclization is generally carried out using catalytic amounts of an acidic catalyst, such as p-toluenesulfonic acid, phophoric acid, oxalic acid or an acidic ion exchanger.

When carbon atoms 4 and 7 are asymmetrically substituted, the novel compounds according to the invention occur in the form of diastereomer mixtures. Because of the rounded notes, separation is not necessary from an olfactory point of view. They may therefore be present in the form of stereoisomers, both as diastereomers and as enantiomers.

The novel 4,7-dihydro-1,3-dioxepins of the formula I can readily be combined with other scents in various proportions to give novel, interesting scent compositions. In addition to being used in fine perfumery, compositions of this type can be employed for perfuming cosmetics, such as creams, lotions, aerosols, toilet soaps and industrial articles such as cleaning agents and detergents, softeners, disinfectants and textile treatment agents.

The 4,7-dihydro-1,3-dioxepins are also important intermediates for further useful scents. For example, they can be converted by hydroformylation to the corresponding 5-formyl-4,7-dihydro-1,3-dioxepins, which constitute a novel class of very interesting synthetic scents.

Compounds of the general formula I which are particularly useful as scents for fine perfumery are:
2-propyl-4,4,7,7-tetramethyl-4,7-dihydro-1,3-diocepin,
2-tert-butyl-4,4,7,7-tetramethyl-4,7-dihydro-1,3-dioxepin,
2,4,4,7,7-pentamethyl-4,7-dihydro-1,3-dioxepin,
2-pentyl-4,4,7,7-tetramethyl-4,7-dihydro-1,3-dioxepin,
2-ethyl-4,4,7,7-tetramethyl-4,7-dihydro-1,3-dioxepin and
2-propyl-4,7-dimethyl-4,7-dihydro-1,3-dioxepin.

The Examples which follow illustrate the subject of the invention.

EXAMPLES 1 TO 15

A mixture of, in each case, 5 moles of the alkenediol shown in Table 1, 3 g of p-toluenesulfonic acid, 5 moles of the carbonyl compound shown in Table 1 and 1 liter of toluene or cyclohexane was refluxed for the reaction time shown in the table, the water of reaction produced being separated off from the reaction mixture. After the mixture had cooled to room temperature, 10 ml of a 25% strength aqeuous NaOH were added, the reaction mixture was washed neutral with a little water, the toluene was distilled off at from 50° to 60° C. and the residue was distilled under reduced pressure. The physical data of the resulting substituted 4,7-dihydro-4-methyl-1,3-dioxepins, and a description of their odor, are given in Table 1.

TABLE 1

| Example | Alkenediol | Carbonyl compound | -4,7-dihydro-1,3-dioxepin | bp. [°C./mbar] | $n_D^{25}$ | Description of odor |
|---|---|---|---|---|---|---|
| 1 | hex-3-ene-2,5-diol | n-butanal | 2-propyl-4,7-dimethyl- | 36/0.4 | 1.4382 | green, grass-like |
| 2 | 2,5-dimethylhex-3-ene-2,5-diol | n-hexanal | 2-pentyl-4,4,7,7-tetramethyl- | 83/0.1 | 1.4450 | green herbaceous note |
| 3 | 2,5-dimethylhex-3-ene-2,5-diol | n-butanal | 2-propyl-4,4,7,7-tetramethyl- | 66/0.1 | 1.4408 | camphor-like with a fennel note |
| 4 | 2,5-dimethylhex-3-ene-2,5-diol | 2,2-dimethylpropanal | 2-tert-butyl-4,4,7,7-tetramethyl- | 47/0.5 | 1.4380 | mint note |
| 5 | 2,5-dimethylhex-3-ene-2,5-diol | acetaldehyde | 2,4,4,7,7-pentamethyl- | 50/0.1 | 1.4362 | L-menthol-like cooling effect |
| 6 | 2,5-dimethylhex-3-ene-2,5-diol | 3,5,5-trimethylhexanal | 2-(2,4,4-trimethylpentyl)-4,4,7,7-tetramethyl- | 81/0.1 | 1.4442 | fresh, ozone-like |
| 7 | 2,5-dimethylhex-3-ene-2,5-diol | 2-methylpropanal | 2-isopropyl-4,4,7,7-tetramethyl- | 36/0.3 | 1.4381 | aniseed-like, fennel-like |
| 8 | hex-3-ene-2,5-diol | n-hexanal | 2-pentyl-4,7-dimethyl- | 57/0.5 | 1.4437 | herbaceous, celery-like |
| 9 | hex-3-ene-2,5-diol | 2-methylundecanal | 2-(1-methyldecyl)-4,7-dimethyl- | 130/0.01 | 1.4470 | weak green note |
| 10 | 2,5-dimethylhex-3-ene-2,5-diol | n-propanal | 2-ethyl-4,4,7,7-tetramethyl- | 34/0.4 | 1.4379 | basil, tarragon-like |
| 11 | 2,5-dimethylhex-3-ene-2,5-diol | methoxyacetaldehyde | 2-methoxymethyl-4,4,7,7-tetramethyl- | 46/0.015 | 1.4431 | herbaceous, fruity |
| 12 | hex-3-ene-2,5-diol | 3-formylpinane | 2-(2,7,7-trimethylbicyclo-[3.1.1$^{1.5}$]hept-3-yl)-4,7-dimethyl- | 78/0.01 | 1.4841 | celery-like |
| 13 | hex-3-ene-2,5-diol | 3-formyltetrahydropyran | 2-(3-tetrahydropyranyl)-4,7-dimethyl- | 95/0.01 | 1.4712 | fresh floral, fruity |
| 14 | hex-3-ene-2,5-diol | cyclopentylcarbaldehyde | 2-cyclopentyl-4,7-dimethyl- | 67/0.08 | 1.4661 | herbaceous, bornal-like |
| 15 | 4-methylpent-2- | 2-methylpropanal | 2-isopropyl-4,4-dimethyl- | 45/0.25 | 1.4472 | fresh green |

TABLE 1-continued

| Example | Alkenediol ene-1,4-diol | Carbonyl compound | -4,7-dihydro-1,3-dioxepin | bp. [°C./mbar] | $n_D^{25}$ | Description of odor |
| --- | --- | --- | --- | --- | --- | --- |

Example of use

The wide range of possible uses of the novel compounds will be illustrated, by way of example, by the effect of 2-pentyl-4,4,7,7-tetramethyl-1,3-dioxacyclohept-5-ene (Example 2) in a green composition (literature: F. V. Wells and M. Billot, Perfumery Technology, 2nd edition, Halsted Press/John Wiley & Sons, New York 1981, page 271).

| Green Bouquet 279 | A | B |
| --- | --- | --- |
| 2-pentyl-4,4,7,7-tetramethyl-4,7-dihydro-1,3-dioxepin | 0 | 7 |
| phenylacetaldehyde 100% | 1.5 | 1.5 |
| phenylacetaldehyde dimethyl acetal | 7 | 0 |
| p-toluylacetaldehyde | 5 | 5 |
| cetone V (allylionone) | 3 | 3 |
| cis-3-hexenol | 3 | 3 |
| methylphenylcarbinyl acetate | 5 | 5 |
| oak moss absolute | 2 | 2 |
| methyl cinnamate | 3 | 3 |
| cinnamic alcohol | 5 | 5 |
| methyl naphthyl ketone | 2 | 2 |
| hydroxycitronellal | 6 | 6 |
| dimethylbenzylcarbinyl acetate | 5 | 5 |
| lilial (Givaudan) | 3 | 3 |
| phenylethyl alcohol | 10 | 10 |
| citronellol | 6 | 6 |
| phenylethyl acetate | 3 | 3 |
| isoeugenol | 3 | 3 |
| ylang-ylang oil | 5 | 5 |
| undecylenaldehyde 10% | 1 | 1 |
| cyclamen aldehyde | 3 | 3 |
| bergamot oil | 3 | 3 |
| lemon oil, guinea | 1.5 | 1.5 |
| galbanum oil | 1 | 1 |
| elemi oil | 1 | 1 |

-continued

| Green Bouquet 279 | A | B |
| --- | --- | --- |
| methyl heptyne carbonate 5% | 2 | 2 |
| Jasmin Base SR | 10 | 10 |
| | 100 | 100 |

Replacing the phenylacetaldehyde dimethyl acetal in Green Bouquet 279 (A) with the novel compound from Example 4 gives the green fantasy blend an even fresher, rounder spicy note.

We claim:

1. A scent composition which contains a substituted 4-methyl-4,7-dihydro-1,3-dioxepin of the formula I

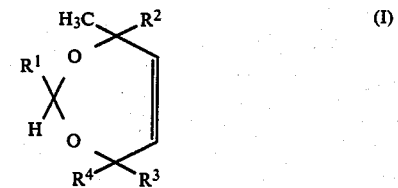

where $R^1$ is a straight-chain or branched alkyl radical of 1 to 12 carbon atoms which may furthermore contain oxygen in the form of an ether group, or a 5-membered to 8-membered ring which is unsubstituted or substituted by alkyl groups and/or an alkylene group, has up to 10 carbon atoms and may furthermore contain oxygen in the form of an ether group, and $R^2$, $R^3$ and $R^4$ are each hydrogen or methyl, the total number of carbon atoms being not more than 25.

2. A scent composition according to claim 1, which contains a 4-methyl-4,7-dihydro-1,3-dioxepin in an amount of from 0.5 to 50% by weight.

* * * * *